(12) United States Patent
Kniewasser

(10) Patent No.: US 7,047,968 B2
(45) Date of Patent: May 23, 2006

(54) DEVICE FOR GENERATING A CONTINUOUS POSITIVE AIRWAY PRESSURE (CPAP DEVICE)

(75) Inventor: Gert Kniewasser, Kaltenber (DE)

(73) Assignee: Med In Medical Innovations GmbH (DE)

( * ) Notice: Subject to any disclaimer, the term of this patent is extended or adjusted under 35 U.S.C. 154(b) by 134 days.

(21) Appl. No.: 10/633,167

(22) Filed: Aug. 1, 2003

(65) Prior Publication Data
US 2004/0020488 A1 Feb. 5, 2004

(30) Foreign Application Priority Data
Aug. 2, 2002 (EP) .................................. 02017388

(51) Int. Cl.
A61M 16/00 (2006.01)
A61M 15/08 (2006.01)
A61M 15/00 (2006.01)

(52) U.S. Cl. .......................... 128/204.18; 128/207.18; 128/203.12; 128/207.14

(58) Field of Classification Search ........... 128/204.18, 128/207.18, 203.12, 207.14
See application file for complete search history.

(56) References Cited

U.S. PATENT DOCUMENTS 3,319,627 A * 5/1967 Windsor ................. 128/204.25
3,653,379 A * 4/1972 Glenn ..................... 128/204.21
3,977,432 A * 8/1976 Vidal .......................... 137/889
4,098,290 A * 7/1978 Glenn ..................... 128/204.25
5,193,532 A * 3/1993 Moa et al. ............... 128/204.25
5,605,148 A * 2/1997 Jones ...................... 128/205.11
5,975,077 A * 11/1999 Hofstetter et al. ...... 128/207.18
6,125,844 A * 10/2000 Samiotes ................ 128/200.23
6,328,030 B1 * 12/2001 Kidwell et al. ......... 128/200.21
6,807,967 B1 * 10/2004 Wood ..................... 128/207.18

FOREIGN PATENT DOCUMENTS
WO   WO 99/24101   * 5/1999

* cited by examiner

Primary Examiner—Henry Bennett
Assistant Examiner—Andrew Bunin
(74) Attorney, Agent, or Firm—F. Chau & Associates, LLC

(57) ABSTRACT

The present invention provides a device for generating a continuous positive airway pressure (CPAP device), in particular a nasal CPAP device (nCPAP device), with a hollow body (10) in which an overpressure can be built up; with a first opening (20) provided in a first side wall of the hollow body (10) and used for introduction of a respiratory gas flow (A) directed into the hollow body (10) and for removal of the exhaled respiratory gas flow (B); and with an attachment piece (30) which can be fitted on the hollow body (10) in order to connect the hollow body (10) to a nosepiece and/or mouthpiece (100). A second opening (71) is provided in a second side wall of the hollow body (10) and is used for introduction of a medicament flow (M) directed into the hollow body (10).

14 Claims, 4 Drawing Sheets

DEVICE FOR GENERATING A
CONTINUOUS POSITIVE AIRWAY
PRESSURE (CPAP DEVICE)

PRIOR ART

The present invention relates to a device for generating a continuous positive airway pressure (CPAP device), and in particular to a nasal CPAP device (nCPAP device), according to the preamble of claim 1, and as known from WO 99/24101.

The principle of these CPAP and nCPAP devices is that the patient breathes against a pressure which is higher than the atmospheric pressure, and, in some cases of impaired pulmonary function, this facilitates and improves spontaneous breathing.

An extremely important application is in the treatment of neonates. The effect in this connection is that the still immature lung is inflated by the overpressure and, as a result, a better exchange of gas is made possible. Another very significant factor is that this technique can be used to avoid the life-threatening collapse of the alveoli caused by the negative respiratory pressure. Another point of interest is that the alveoli are opened more effectively, and in this way the overall functional status of the lungs is improved.

EP-A-0 658 356 discloses a CPAP device with a pair of nose attachments each provided with a cannula tip for insertion into the patient's nostrils.

DE-C-3 119 814 discloses a CPAP or nCPAP device with a breathing channel which at its free end is open to the atmosphere and at its other end can be provided with a coupling piece for fitting on the patient's nose and/or mouth, and with an inlet channel for fresh gas, said inlet channel being connected to the breathing channel, at a location between the ends of the latter, and its through-flow being adjustable.

EP 0 447 443 B1 discloses a development of this known CPAP or nCPAP device where the breathing channel has a first branch channel which can be connected to the coupling piece, and a second branch channel which is open to the atmosphere. The two breathing channels form an angle with one another, so that the inlet channel lies substantially in the continuation of the first branch channel and is connected to the second branch channel in such a way that the stream of fresh gas is oriented mainly coaxially in the first branch channel and thus produces an ejection action. The cross-sectional area of the respective branch channel is several times greater than the smallest cross-sectional area of the inlet channel, and the length of each branch channel is relatively short and is preferably five times its internal diameter. The breathing channel is constructed together with the inlet channel as a compact unit which can be fitted to the patient's nose and/or mouth using a tape or suitable means.

FIG. 3 shows a diagrammatic representation, in a perspective view, of a CPAP device which is known from WO 99/24101.

The main components of this known device for generating a continuous positive airway pressure are a cylindrical hollow body 10 in which an overpressure can be built up; a first opening 20 provided in the circumferential surface of the cylindrical hollow body 10 and used for introduction of a respiratory gas flow A directed into the hollow body 10 and for removal of the exhaled respiratory gas flow B; an attachment piece 30 which can be fitted on the cylindrical hollow body 10, on one end surface 10a thereof, in order to connect the hollow body 10 to a nosepiece and/or mouthpiece 100, as is explained in more detail in FIGS. 4 and 5; and a spacer 40 which can be fitted on the hollow body 10 and on which a flow nozzle 50 for directing the respiratory gas flow A to the opening 20 can be arranged.

The attachment piece 30 consists of a stopper made of Teflon which can be at least partially inserted into the hollow body 10 at the end surface 10a. This stopper is expediently designed as a stepped part that can be turned. It has two passages (broken lines) which correspond to corresponding respiratory gas passages in the nosepiece 100. Two outwardly pointing pipe stubs 35 for introduction into the nosepiece and/or mouthpiece 100 are provided in the passages of the attachment piece 30.

Through its design as a stopper, the attachment piece 30 can be turned relative to the hollow body 10 about the cylinder axis, which lies substantially perpendicular to the axis of the respiratory gas flow A directed into the hollow body 10.

Provided on the other end surface 10b of the cylindrical hollow body 10 there is a second opening for connection of a pressure gauge. For this purpose, a pipe 60 for attachment to a pressure gauge line is connected substantially at a right angle to the second opening using a reinforcement plate (not shown) arranged in the hollow body 10 in the end surface 10b.

The pipe 60 extends substantially by the same length from the hollow body 10 as does the flow nozzle 50, so that a line for delivering pressurized respiratory gas to the flow nozzle can be arranged on the flow nozzle 50 substantially at the same height as the pressure gauge line.

In the illustrative embodiment shown, the hollow body 10, the spacer 40, the flow nozzle 50, the pipe 60, the reinforcement plate and the pipe stubs 35 are made of aluminum or fine aluminum.

The spacer 40 is in this case fitted securely on the hollow body 10 by flanging with an inserted ring. In addition, the flow nozzle 50 is fitted securely on the spacer 40 by screwing. Finally, the pipe 60 is fitted securely and in a leaktight manner on the hollow body 10 by flanging or screwing. A pipe 75 sealingly connected to flow nozzle 50 supplies gas from a compressed air generator.

Alternatively, the pipe 60 could be fitted so as to be able to turn relative to the hollow body 10 about at least one defined axis, in which case care must be taken to ensure appropriate leaktightness, as with the attachment piece 30.

The spacer 40 has a substantially annular shape. The flow nozzle 50 is guided through a hole in the side wall of the annular shape and is oriented substantially perpendicular to the opening 20. The flow nozzle 50 protrudes by a predetermined length into the inside of the annular shape.

The side wall of the annular shape has a safety opening 45 for respiratory gas. The annular shape of this construction can be closed with the fingers, so that the exhaled respiratory gas flow B passes through the safety opening 45 for respiratory gas.

FIG. 4 shows a first cross-sectional view of a nosepiece for connection to the attachment piece in FIG. 3.

The nosepiece 100 shown is made of very soft silicone. It has a central part 150 in the form of a cuboid with two holes 151, 152, and two thin-walled nose inserts 153, 154 issuing from these holes and directed upward from the plane of the drawing. Arranged on both sides of the cuboid there are tabs 160, 170 which can be secured on the patient's head by means of a tape or corresponding means which can be guided through corresponding holes 165, 175.

FIG. 5 shows a second cross-sectional view of the illustrative embodiment of a nosepiece for connection to the attachment piece, along the line A–A' indicated in FIG. 4.

The nosepiece 100 is also preferably a disposable part, because silicone hardens on autoclaving and could thus injure the patient's nostrils.

The function and the constructional details of this known CPAP device are explained in more detail below.

The sizes are typically as follows:

| | |
|---|---|
| Length of hollow cylinder | 15 mm |
| Diameter of hollow cylinder | 15 mm |
| Diameter of annular spacer | 10 mm |
| Width of annular spacer | 10 mm |
| Length of flow nozzle | 15 mm, of which 5 mm within the annular spacer |
| Diameter of first opening | 5 mm |
| Diameter of safety opening for respiratory gas | 3 mm |
| Length of pipe stubs | 5 mm |
| Diameter of pipe stubs | 2 mm |
| Width of nosepiece block | 15 mm |
| Height of nosepiece block | 5 mm |
| Depth of nosepiece block | 10 mm |
| Length of tabs | 17 mm |

The respiratory gas flow delivered through the flow nozzle 50 typically amounts to 10 to 15 liters per minute. An overpressure proportional to this is thus built up in the cylindrical hollow space 10. The larger the first opening 20, the lower the overpressure that is built up. The aim is to achieve an exact balance between the amount of gas delivered, the volume of the cylinder and the diameter of the first opening, so that, during respiration, as far as possible no respiratory gas from the environment is delivered which could shift the $O_2$ concentration. Moreover, the outlets to the nosepiece are also optimized so that the least possible dead space exists upon breathing.

In the simplest case, the pressure gauge used can be a water column gauge with water lock; otherwise, it is of course also possible to use more complicated electronic gauges. All the conventional gas propulsion apparatus can be used as the device for generating compressed respiratory gas. It should be noted that using two pipe interfaces, one for the pressure measurement and one for the gas delivery, ensures a substantially free choice in the selection of these two apparatus.

The safety opening for respiratory gas located on the annular spacer has an important function. If the annular spacer is closed at both sides with the fingers, this results in an immediate increase in pressure. This is used to inflate the lungs. However, the safety opening for respiratory gas limits the pressure to a predetermined value, which depends in particular on the diameter of the safety opening. If the CPAP device is run with the above measurements and the pressure during normal operation corresponds to a water column of 5 cm, then an increase to a water column of 12 cm is obtained by closing the annular spacer at the sides.

It is also known that, in the respiratory treatment of neonates, additional treatment with medication is often required. For this purpose, separate ancillary masks with upstream medication atomizers are known. A disadvantage of these has been the fact that the respiratory treatment of the neonates has to be interrupted for the additional treatment with medication.

Attempts at coupling an atomizer between the compressed air generator and the device according to FIG. 3 led to unsatisfactory results, among other reasons because undesired condensation occurred as a result of the exhaled respiratory gas flow B, which is warmer than the inhaled respiratory gas flow A.

The problem which the present invention aims to solve is therefore generally that of developing a device of the generic type for producing a continuous positive airway pressure (CPAP device), and in particular a nasal CPAP device (nCPAP device), in such a way that the respiratory treatment of neonates does not have to be interrupted to provide additional treatment with medication.

ADVANTAGES OF THE INVENTION

Compared to the known solutions, the CPAP or nCPAP device according to the invention, with the features of claim 1, has the advantage that the respiratory treatment of neonates and the additional treatment with medication can be carried out simultaneously and in synergy, without causing undesired condensation effects.

The idea on which the present invention is based is that a second opening is provided in a second side wall of the hollow body and is used for introduction of a flow of medicament directed into the hollow body.

Advantageous developments and improvements of the nCPAP device specified in claim 1 are set out in the dependent claims.

According to a preferred development, a spacer is provided which can be fitted on the hollow body and on which a flow nozzle for directing the respiratory gas flow to the first opening can be arranged.

According to a further preferred development, the hollow body basically has the shape of a hollow cylinder on whose one end surface the attachment piece can be fitted and on whose circumferential surface the first and second openings are provided.

According to a further preferred development, the first and second openings lie at approximately the same height, so that the respiratory gas flow directed into the hollow body and the medicament flow directed into the hollow body at least partially intersect in an area. This arrangement affords an additional vortex effect.

According to a further preferred development, a pipe is inserted into the second opening and protrudes into the inside of the hollow body.

According to a further preferred development, the pipe protrudes so far into the inside of the hollow body that it forms a break-up edge for the respiratory gas flow directed into the hollow body. This break-up edge ensures an additional vortex.

According to a further preferred development, the pipe can be plugged in. It is therefore easy to remove and fit when necessary.

According to a further preferred development, the second opening can be closed off by a closure means, preferably a lid or slide.

According to a further preferred development, the first and second openings are arranged at an acute angle to one another on the circumferential surface.

According to a further preferred development, the attachment piece consists of a stopper which can be at least partially inserted into the hollow body at the end surface. Preferably, neither of the two flows, namely the respiratory gas flow or the medicament flow, is oriented directly to the attachment piece.

According to a further preferred development, the attachment piece has one or two passages which correspond to corresponding respiratory gas passages of the nosepiece and/or mouthpiece.

According to a further preferred development, one or two outwardly pointing pipe stubs for introduction into the nosepiece and/or mouthpiece are provided in the passages of the attachment piece.

According to a further preferred development, the attachment piece can be turned relative to the hollow body about at least one defined axis and has a closure means with which the second opening can be closed by said turning. This closure means could, for example, be a protruding tab or flap.

According to a further preferred development, the defined axis (cylinder axis) lies substantially perpendicular to the axis of the respiratory gas flow and medicament flow directed into the hollow body. This results in a rebound effect on the cylinder wall, which effect assists in thorough mixing.

According to a further preferred development, the spacer has a substantially annular or cup-shaped configuration.

According to a further preferred development, the flow nozzle is guided through a hole in the side wall of the annular shape or cup shape and is oriented substantially perpendicular to the first opening.

According to a further preferred development, the flow nozzle projects by a predetermined length into the inside of the annular shape or inside of the cup shape.

According to a further preferred development, a third opening for attachment of a pressure gauge is provided in one side wall of the hollow body, preferably a side wall different than the side wall with the first opening.

DRAWINGS

Illustrative embodiments of the invention are shown in the drawings and are explained in more detail in the following description.

DESCRIPTION OF THE ILLUSTRATIVE EMBODIMENTS

In the figures, identical reference numbers designate identical or functionally similar elements.

Figure 1:
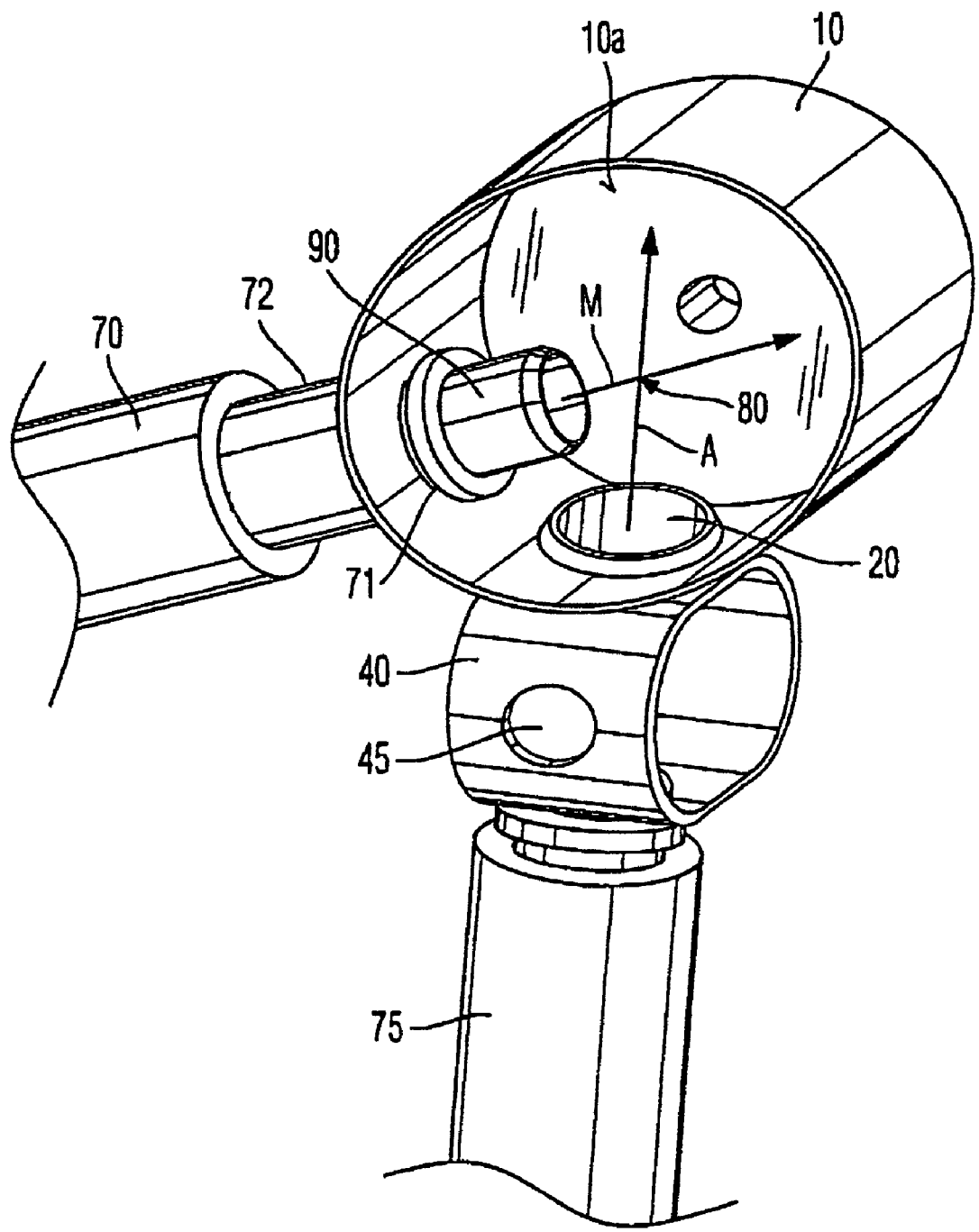
FIG. 1 shows a diagrammatic representation of an embodiment of the CPAP device according to the invention, in a first perspective view.
Figure 2:
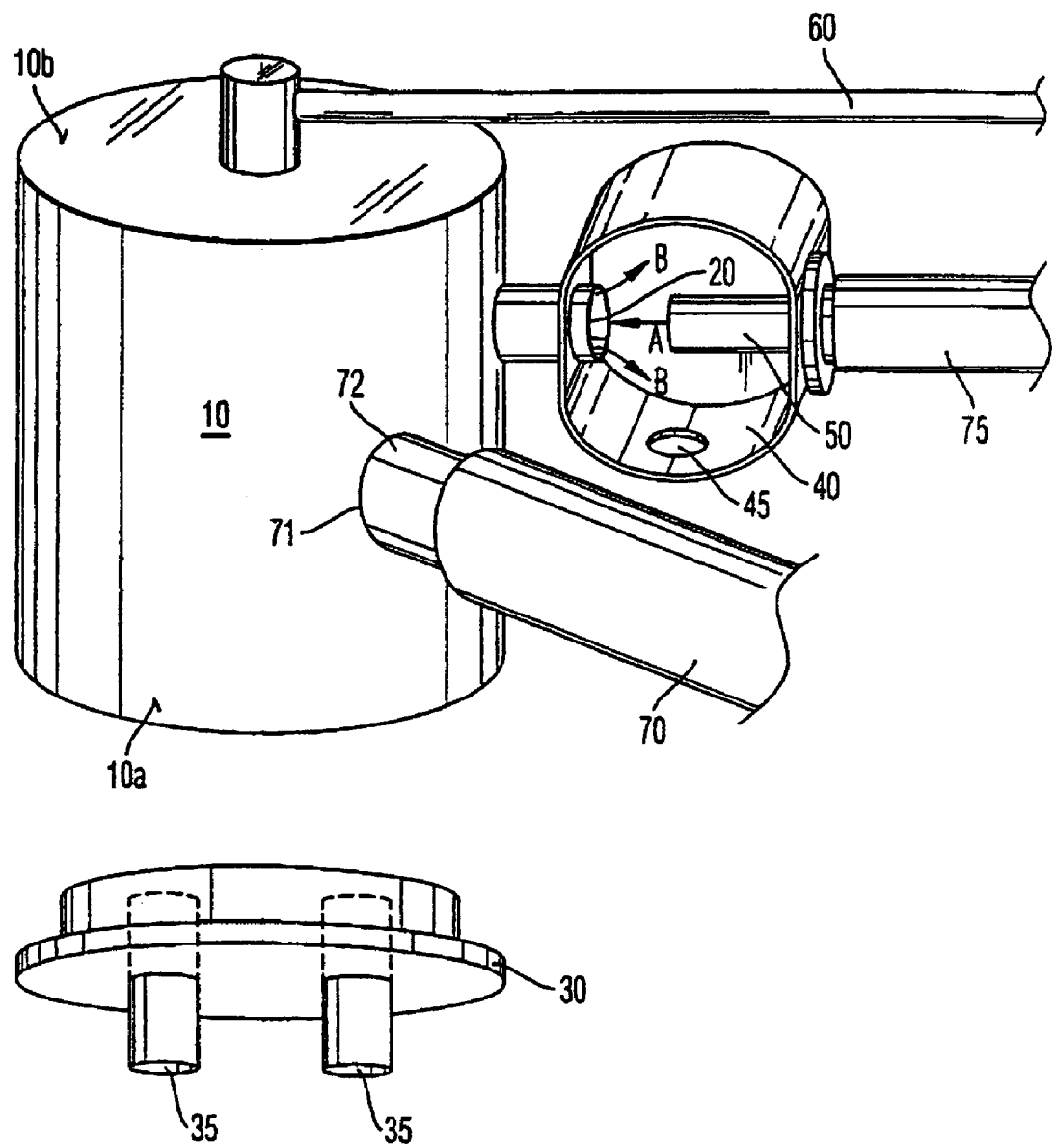
FIG. 2 shows a diagrammatic representation of the embodiment of the CPAP device according to the invention, in a second perspective view.

FIG. 1 shows a diagrammatic representation of an embodiment of the CPAP device according to the invention, in a first perspective view, and FIG. 2 shows it in a second perspective view.

Figure 3:
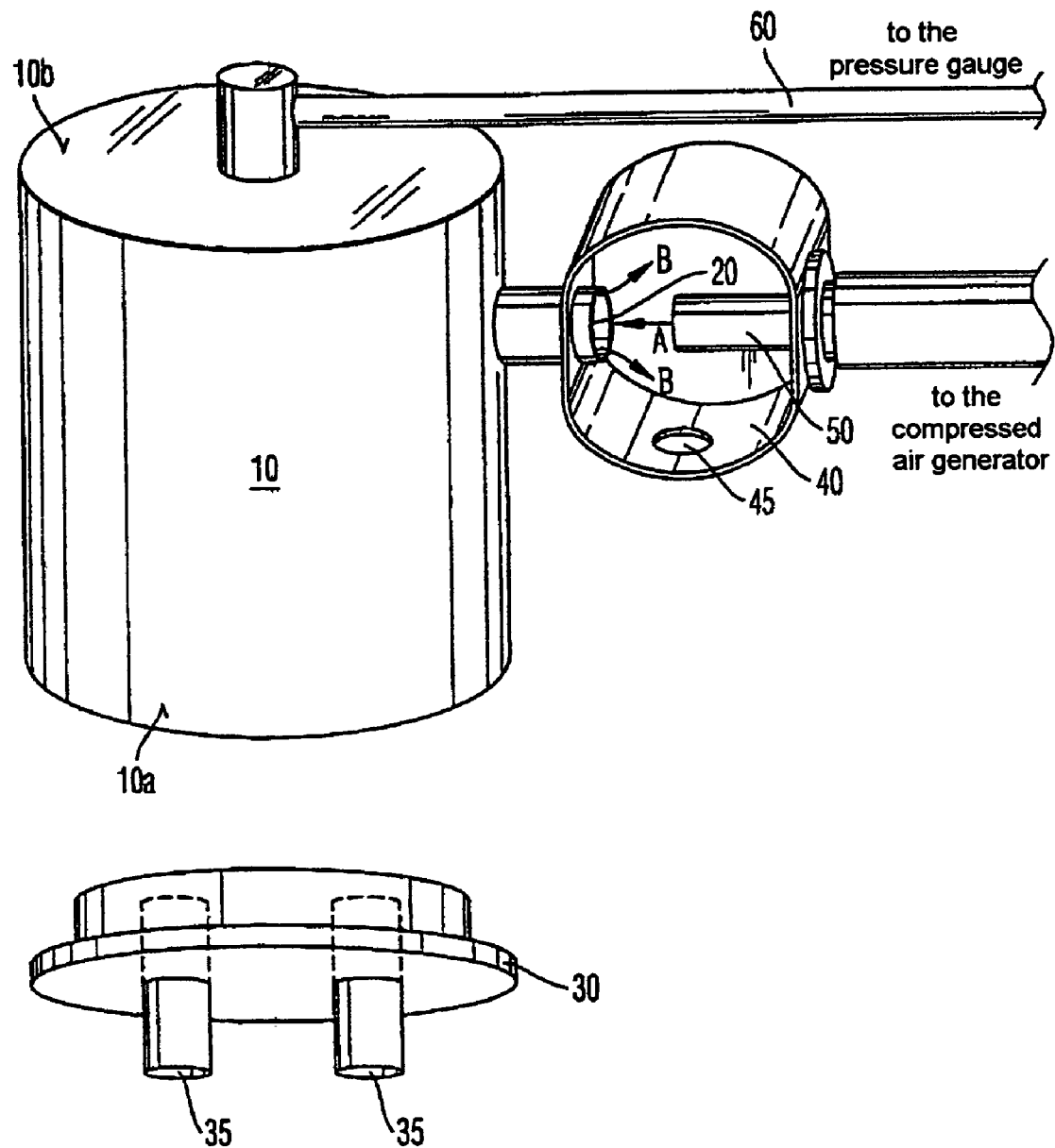
FIG. 3 shows a diagrammatic representation of a CPAP device known from WO 99/24101, in a perspective view.
Figure 4:
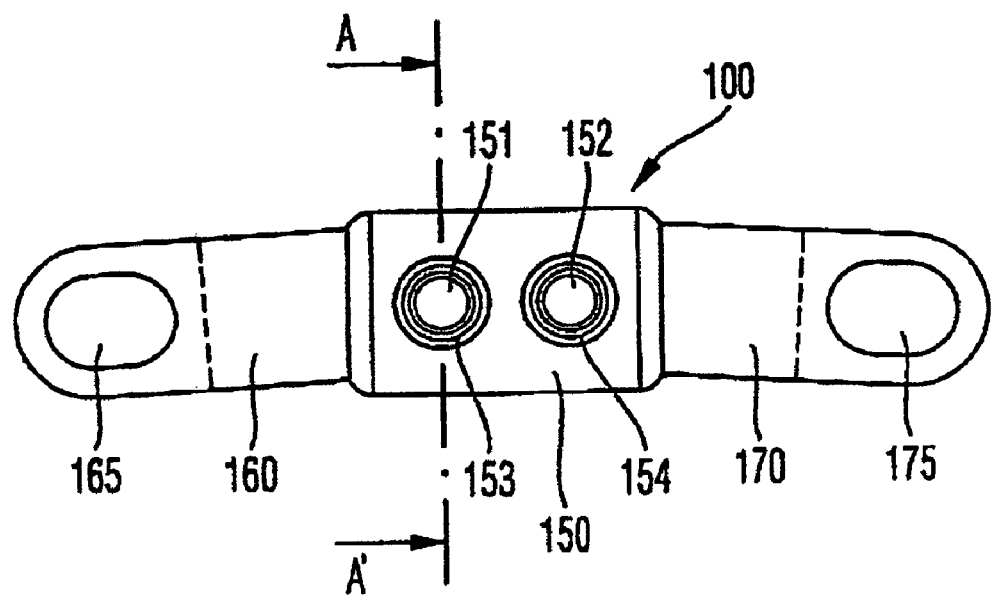
FIG. 4 shows a first cross-sectional view of a nosepiece for connection to the attachment piece of FIG. 3.
Figure 5:
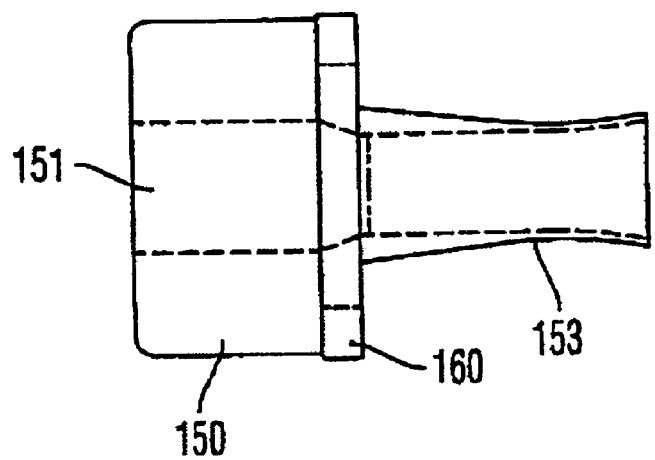
FIG. 5 shows a second cross-sectional view of the nosepiece for connection to the attachment piece, along the line A–A' indicated in FIG. 4.

The main components of this embodiment of the device according to the invention for generating a continuous positive airway pressure are the same as those which were discussed in the introduction with reference to FIGS. 3 to 5.

This illustrated device for generating a continuous positive airway pressure (CPAP device), in particular a nasal CPAP device (nCPAP device), thus also comprises the hollow body 10 in which an overpressure can be built up.

The first opening 20 for introduction of a respiratory gas flow A directed into the hollow body 10 and for removal of the exhaled respiratory gas flow B is provided in a first side wall of the hollow body 10. The same attachment piece 30 for connecting the hollow body 10 to the nosepiece and/or mouthpiece 100 can be arranged on the hollow body 10.

A second opening 71 is additionally provided in a second side wall of the hollow body 10 and is used for introduction of a medicament flow M directed into the hollow body 10, which medicament flow comes, for example, from a disposable atomizer (not shown) arranged upstream.

The first and second openings 20, 71 are provided at an acute angle on the circumferential surface of the cylinder. Thus, in this example, the first side wall is the same as the second side wall. This is advantageous as regards the mixing effect, but does not necessarily have to be the case.

The first and second openings 20, 71 lie at approximately the same height, so that the respiratory gas flow A directed into the hollow body 10 and the medicament flow M directed into the hollow body 10 intersect at an area 80 before they impact the inner wall of the hollow cylinder. This results in an advantageous vortex effect and atomization.

A pipe 90 is inserted into the second opening 71 such that it can be removed therefrom, said pipe projecting into the inside of the hollow body 10 and, on the outside, merging into an attachment piece 72 onto which a tube 70 can be fitted.

In this example, the pipe 90 projects into the inside of the hollow body 10 so far that it forms a break-up edge for the respiratory gas flow A directed into the hollow body 10. This is not absolutely necessary but assists in obtaining the vortex effect.

Although not shown, the second opening 71 can be closed off by a closure means in the form of a lid. In this way, the medicament port can be closed off and/or connected up as and when required.

By means of this construction, respiratory treatment of neonates and additional treatment with medication can be carried out during operation simultaneously and in synergy, without causing undesired condensation effects. If there is no requirement for additional treatment with medication, the pipe 90 is simply unplugged and the hollow body closed.

Although the present invention has been described above on the basis of a preferred illustrative embodiment, it is not limited thereto, and instead it can be modified in a large number of ways.

The closure function could also be realized using a slide arranged in the inside or on the outside of the hollow body 10. The attachment piece 30 which can be turned relative to the hollow body 10 about the cylinder axis could also have and [sic] a closure means in the form of an extension at the lower periphery, by means of which the second opening 71 can be closed by turning.

In particular, the dimensions can be chosen according to the specific requirements. The hollow space can also have any other desired shape than the cylinder shape.

What is claimed is:

1. Device for generating a continuous positive airway pressure (CPAP device), in particular a nasal CPAP device (nCPAP device), with:
   a hollow body (10) in which an overpressure can be built up;
   a first opening (20) provided in a first side wall of the hollow body (10) and used for introduction of a respiratory gas flow (A) under said overpressure directed into the hollow body (10) and for removal of the exhaled respiratory gas flow (B); and an attachment piece (30) which can be fitted on the hollow body (10) in order to connect the hollow body (10) to a nosepiece and/or mouthpiece (100);

characterized by a second opening (71) provided in a second side wall of the hollow body (10) and used for introduction of a medicament flow (M) directed into the hollow body (10).

2. Device according to claim 1, characterized in that a spacer (40) is provided which can be fitted on the hollow body (10) and on which a flow nozzle (50) for directing the respiratory gas flow (A) to the first opening (20) can be arranged, the hollow body (10) basically has the shape of a hollow cylinder on whose one end surface (10a) the attachment piece (30) can be fitted and on whose circumferential surface the first and second openings (20; 71) are provided, the first and second openings (20; 71) lie at approximately the same height, so that the respiratory gas flow (A) directed into the hollow body (10) and the medicament flow (M) directed into the hollow body (10) at least partially intersect in an area (80) before they impact the inner wall, and a pipe (90) is inserted into the second opening (71) and projects so far into the inside of the hollow body (10) that it forms a break-up edge in the interior with an offset to the wall of the hollow body for the respiratory gas flow (A) directed into the hollow body (10).

3. Device according to claim 2, characterized in that the pipe (90) can be plugged in.

4. Device according to claim 1, characterized in that the second opening (71) can be closed off by a closure means, preferably a lid or slide.

5. Device according to claim 2, characterized in that the first and second openings (20; 71) are arranged at an acute angle to one another on the circumferential surface.

6. Device according to claim 2, characterized in that the attachment piece (30) consists of a stopper which can be at least partially inserted into the hollow body (10) at the end surface (10a).

7. Device according to claim 2, characterized in that the attachment piece (30) has one or two passages which correspond to corresponding respiratory gas passages of the nosepiece and/or mouthpiece (100).

8. Device according to claim 7, characterized in that one or two outwardly pointing pipe stubs (35) for introduction into the nosepiece and/or mouthpiece (100) are provided in the passages of the attachment piece (30).

9. Device according to claim 1, characterized in that the attachment piece (30) can be turned relative to the hollow body (10) about at least one cylinder axis and has a closure means with which the second opening (71) can be closed by said turning.

10. Device according to claim 9, characterized in that the cylinder axis lies substantially perpendicular to the axis of the respiratory gas flow (A) and medicament flow (M) directed into the hollow body (10).

11. Device according to claim 2, characterized in that the spacer (40) has a substantially annular or cup-shaped configuration.

12. Device according to claim 11, characterized in that the flow nozzle (50) is guided through a hole in the side wall of the annular shape or cup shape and is oriented substantially perpendicular to the first opening (20).

13. Device according to claim 12, characterized in that the flow nozzle (50) projects by a predetermined length into the inside of the annular shape or inside of the cup shape.

14. Device according to claim 1, characterized in that a third opening for attachment of a pressure gauge is provided in one side wall of the hollow body (10), preferably a side wall different than the side wall with the first opening (20).

* * * * *